United States Patent
Yang et al.

(10) Patent No.: US 8,199,995 B2
(45) Date of Patent: Jun. 12, 2012

(54) SENSITOMETRIC RESPONSE MAPPING FOR RADIOLOGICAL IMAGES

(75) Inventors: Chang-Ying Joseph Yang, Webster, NY (US); Zhimin Huo, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 1062 days.

(21) Appl. No.: 12/021,504

(22) Filed: Jan. 29, 2008

(65) Prior Publication Data
US 2009/0190716 A1 Jul. 30, 2009

(51) Int. Cl.
*G06K 9/78* (2006.01)
(52) U.S. Cl. ......... 382/132; 382/128; 382/131; 382/276
(58) Field of Classification Search .................. 382/128, 382/131, 132, 181, 276, 277, 278, 302
See application file for complete search history.

(56) References Cited

U.S. PATENT DOCUMENTS

| | | | | |
|---|---|---|---|---|
| 5,590,261 A | * | 12/1996 | Sclaroff et al. | 345/473 |
| 2003/0161518 A1 | * | 8/2003 | Vuylsteke | 382/128 |
| 2005/0259882 A1 | * | 11/2005 | Dewaele | 382/243 |
| 2007/0165942 A1 | * | 7/2007 | Jin et al. | 382/154 |

* cited by examiner

*Primary Examiner* — David A Vanore
*Assistant Examiner* — Nicole Ippolito

(57) ABSTRACT

A method for mapping radiological image data from a source imaging system to a target imaging system obtains sensitometric response data for both the source and the target imaging systems and identifies an anchor point that relates a specified source signal value to a specified target signal value. A transform is applied to map a range of source signal values to a corresponding range of target signal values, wherein the transform is defined according to the sensitometric response data obtained for both the source and the target imaging systems and according to the identified anchor point.

8 Claims, 7 Drawing Sheets

SENSITOMETRIC RESPONSE MAPPING FOR RADIOLOGICAL IMAGES

FIELD OF THE INVENTION

The invention relates generally to radiological images and more particularly to a method for correlating image data obtained from different radiographic imaging systems.

BACKGROUND OF THE INVENTION

For many years, conventional radiography employed photosensitive silver-halide film medium for recording images of human and animal tissue. Then, in order to take advantage of advances in digital image processing, many radiographic images originally recorded on film were digitized in order to provide these images in digital data format. This image data could then be analyzed by sophisticated imaging algorithms capable of detecting various conditions that might not be easily be discerned from the film image, even by the trained eye of a skilled diagnostician. A considerable amount of research and development effort has been expended over the last several years to develop and refine image processing algorithms that assist the diagnostician in assessing digitized images. These methods include algorithms capable of detecting conditions evidenced by very subtle effects in an image, such as in mammography and bone-marrow density (BMD) radiography.

More recent advances in imaging technology have made it possible to obtain radiographic images directly as digital data, without the use of photosensitive film. Digital imaging can be performed using Computed Radiography (CR) apparatus that scans and records image data on an erasable sheet of stimulable storage phosphors or using direct Digital Radiography (DR) that obtains image data directly from radiation received from a stimulable storage phosphor. Digital imaging apparatus of these types are particularly advantaged for their wider dynamic range over conventional film imaging. These different film, CR, and DR imaging modalities differ from each other due the different imaging technologies used. Moreover, even within the same imaging modality, there can be differences in results between systems provided by different equipment manufacturers.

Although digital imaging techniques enjoy some advantages over earlier film-based imaging, there are some drawbacks. One of these drawbacks relates to differences in sensitometric response between photosensitive film that is scanned and digitized and the receiver media that are used for obtaining digital data using CR or DR methods. Sensitometric response for a radiographic imaging system is defined in terms of the amount of output signal that is obtained for a given amount of radiation. This sensitometric response for film and digital systems differs significantly in how it is expressed in terms of the output signal level.

For conventional film-based radiography, sensitometric response is plotted as a curve relating Density to the log Exposure. FIG. 1 shows the characteristic sensitometric response of conventional photosensitive film, such as that used in X-ray imaging. This familiar "sigmoid" relationship of the log of incident radiation to the optical density is well known to those skilled in the imaging arts. The schematic diagrams of FIGS. 2A and 2B show what happens in a more general sense. For conventional photosensitive film, the sensitometric response relates the log of the amount of radiation received (conventionally plotted along the abscissa or x-axis of the graph) with the optical density or signal value that is obtained (conventionally plotted along the ordinate or y-axis of the graph). As shown again in FIG. 2A, film shows a sigmoid response curve, wherein the signal value relates to optical density (OD). As shown in FIG. 2B, digital modalities typically exhibit some other characteristic response, including a more linear response when plotted against a value of the incident radiation, and provide an altogether different type of signal value.

As a result of this difference between film and digital systems with respect to what can be considered "signal space" or "recording space", algorithms that were originally developed and fine-tuned for scanned and digitized image data (that is, data obtained from scanned film and exhibiting the sigmoid sensitometric response of film) require some transformation of image data obtained from a CR or DR receiver. Considered more generally, film and digital signal spaces are not identical. Utilities and tools that are developed for one type of imaging modality often do not perform well when used with images of some other type. Thus, the potential value of these diagnostic image analysis tools, developed and perfected for scanned film signal space over years of effort and ongoing research, can be diluted or even lost with the transition to digital receivers. Thus, for example, the same algorithm that automatically detects a lesion or other problem condition from scanned film data is unusable for CR or DR receiver data.

There is, then, a need for a method that provides signal space mapping between the image data obtained using different imaging modalities, effectively converting image data between various types. Suitable methods are needed not only for data transformation between film and digital receiver types, but also between digital receiver types themselves, and even between the same types of digital receivers provided from different systems and manufacturers. Given more accurate signal space mapping, image analysis algorithms and tools that were originally developed and trained for application to data in one imaging modality can be readily used, without significant adjustments, with data from an alternate imaging modality.

SUMMARY OF THE INVENTION

An object of the present invention is to address the difficulties described earlier in the background section. In one embodiment, the present invention provides a method for mapping radiological image data from a source imaging system to a target imaging system comprising: obtaining sensitometric response data for both the source and the target imaging systems; identifying an anchor point that relates a specified source signal value to a specified target signal value; and applying a transform to map a range of source signal values to a corresponding range of target signal values, wherein the transform is defined according to the sensitometric response data obtained for both the source and the target imaging systems and according to the identified anchor point.

An advantage of the present invention is that it provides a signal mapping method that can be adapted for mapping image data between different imaging modalities.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings.

DETAILED DESCRIPTION OF THE INVENTION

It is useful to clarify a number of terms that are used throughout the following detailed description and claims. The term "digitized data" refers to image data that originates with an image formed on a photosensitive film medium. In conventional x-ray workflow, an x-ray image is obtained on a sheet of film, is developed, and is then scanned to convert the film image into digitized data for processing and storage. The scanning process is carried out on a screened film or scanned film (SF) system. In conventional terminology, this data is said to be in digitized data space. In the context of the present disclosure, the label DV denotes values in this Digitized Value space (DV space).

In contrast, the term "digital receiver data" refers to digital data signals obtained directly from a digital receiver, such as that provided in a CR or DR system. This data is said to be in digital receiver data space. In the context of the present disclosure, the label PV denotes pixel values or pixel data values in this CR or DR digital receiver space (PV space).

The term "tone scale curve" is used herein, as in the imaging arts in general, to describe a characteristic relationship of tone scale to image pixel values for images obtained on film. For digitized data from scanned film, each pixel value has a corresponding tone scale value.

The method of the present invention provides a mapping between a "source" system and a "target" system. The source data can be in either DV space or PV space. The target data can be in either DV space or PV space. The following source→target mappings are of particular interest:

(i) PV space→DV space;
(ii) DV space→PV space; and
(iii) PV space (system #1)→PV space (system #2).

Figure 2:
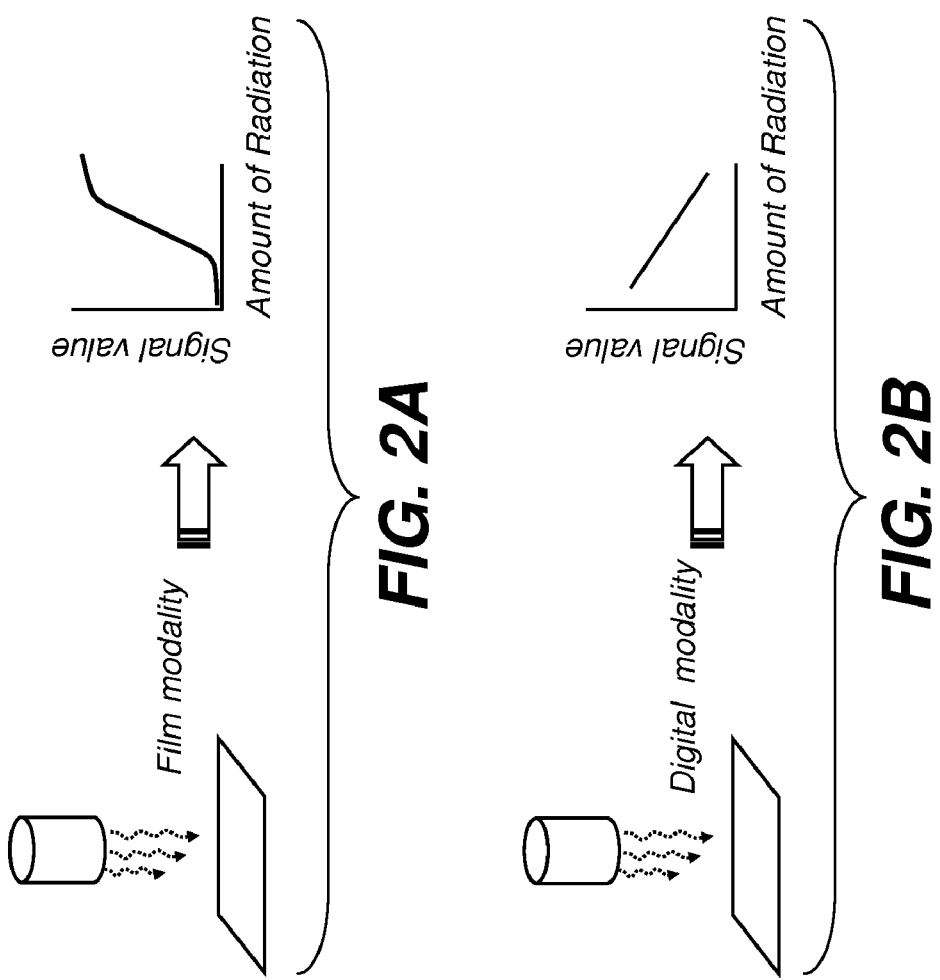
FIGS. 2A and 2B are schematic diagrams showing some typical sensitometric response characteristics of different imaging modalities.

The present Background of the Invention describes problems related to differences in signal space for film and digital receivers. Because the types of signal values obtained from the receiver for these modalities are not the same, there is still further complexity to this problem than FIGS. 2A and 2B show, caused by the additional transformation that is performed in order to digitize the film image and form digitized data (DV values) as just described. Subsequent description shows how the method of the present invention works to map DV data to digital receiver (PV) signal space, as well as to map one type of digital receiver space to another.

Figure 1:
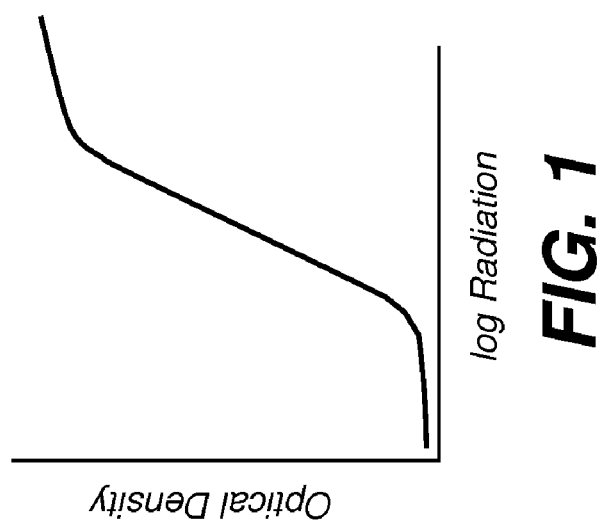
FIG. 1 is a graph showing the characteristic response of photosensitive film to received radiation.

The method of the present invention also provides a transformation mechanism that can be used for improved visualization of radiographic images, whether the images originate from a digital receiver or are digitized from scanned film. This method can also be used to transform digital receiver data to the conventional film-based signal space that was described earlier with reference to FIG. 1. The digital receiver data can be transformed either to Optical Density (OD) form or to Digitized Value (DV) space, depending on which representation is more appropriate for display use or for use of an imaging algorithm.

The detailed first example described in this section is directed to an embodiment that maps source image data from digital receiver image space to scanned film (digitized data) image space as the target imaging system. In terms given earlier, this is a source→target mapping of type (i) PV space→DV space. However, the same overall procedures can apply for transformations to digital target imaging systems, including mapping data from one digital receiver space to another or mapping data from film images space to digital receiver space.

For a better understanding of the procedural sequence that follows, it is important to understand that current digital receivers (CR or DR) provide digital receiver data that has either of two characteristic proportions relative to the amount of x-ray radiation that is received:

i) a substantially linear response to the x-ray radiation level; or ii) a substantially logarithmic response to the x-ray radiation level.

As is shown subsequently, the sequence of procedures that are used for transformation depends, in part, on which receiver response characteristic applies.

Figure 3:
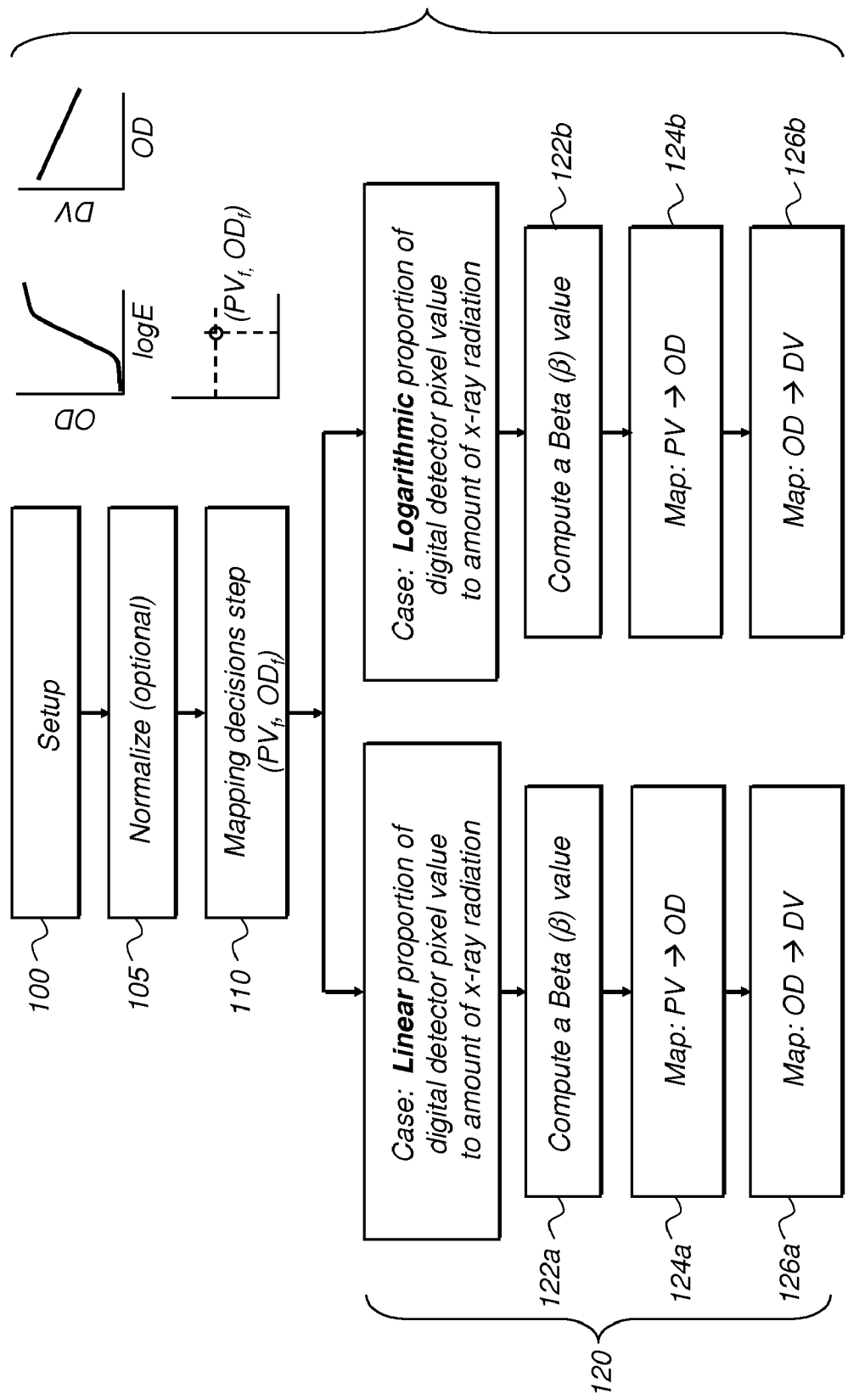
FIG. 3 is a logic flow diagram showing steps used for transformation according to some of the embodiments of the present invention.

The logic flow diagram of FIG. 3 shows a sequence of overall steps that can be used for the method of the present invention in various embodiments. A setup step 100 defines and sets up a model or "ideal" target system. In practice, this is often the system for which Computer-Aided Diagnostics (CAD) algorithms have been optimized. Image data that is re-mapped to this target system can be more favorably processed by such imaging algorithms.

Where the target imaging system uses film, the sensitometric response curve of the target screen film (SF) is obtained. This curve relates logarithmic value of the amount of x-ray radiation to Optical Density (OD) of the film, as was described earlier with reference to the curve of FIG. 1. This sensitometric curve is then fit with a sigmoid function, using:

$$OD = OD_{min} + \frac{a}{b + e^{-c \log_q(R)}} \qquad (\text{eq. 1})$$

where:
OD is the Optical Density of the film that is scanned;
$OD_{min}$ is the value of lowest optical density;
a, b, and c are constants from the fitting process, empirically determined;
for the sensitometric response of the SF system;
R represents the amount of incident x-ray radiation; and
q is the base of the logarithmic function.

Figure 4:
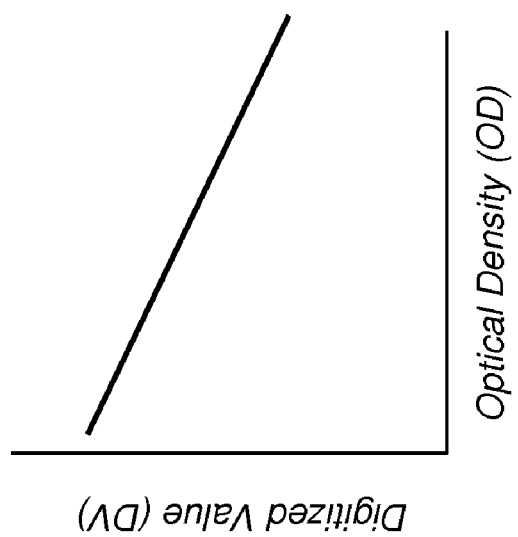
FIG. 4 is a graph showing a linear relationship of digitized value to optical density for a scanning apparatus or other type of digitizer.

As another part of setup step 100, the response curve for the digitizer (scanner) of the target SF system is obtained. This curve shows the output digitized value (DV) from the digitizer as a function of the optical density (OD) of the scanned film. As FIG. 4 shows, the relationship of digitized value to optical density may be substantially linear, so that it can be expressed using:

$$\text{digitized value} = m \times OD + p \qquad (\text{eq. 2})$$

where m and p are both fitting constants, m corresponding to the slope and p analogous to the y-intercept.

Still referring to FIG. 3, an optional normalization step 105 may follow setup, as a preprocessing step for applications in which data from different digital detectors is used. This can be done after determining the sensitivity of the digital detectors. With normalization, the selection of pixel value $PV_f$, as described subsequently, can be more robust. Techniques for normalization of data ranges for different digital detectors are known to those skilled in the diagnostic imaging arts.

Obtaining an Anchor Point

A mapping decisions step 110 follows, in which a pivotal mapping parameter for the image data transformation is identified as a single anchor point that directly or indirectly relates a source pixel code value (PV) to a target optical density value (OD) or digitized value (DV), with coordinates represented as $(PV_f, OD_f)$ or, alternately, $(PV_f, DV_f)$.

Figure 5:
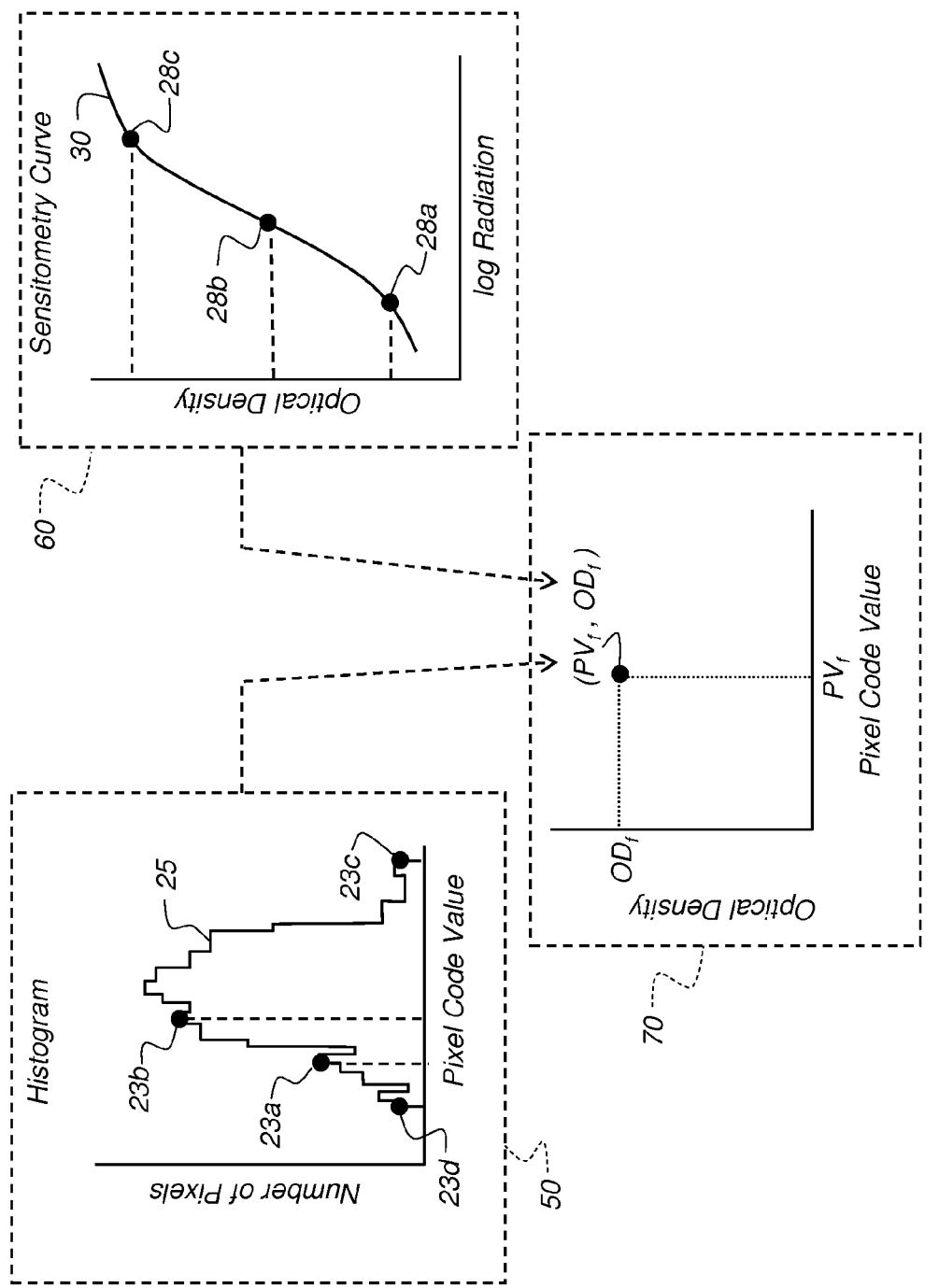
FIG. 5 is a schematic diagram showing how an anchor point for the transform is obtained.

The signal space information that is obtained on film sensitometric response and on the response of the digitizer enables characterization of the target system for mapping of the digital receiver data. The graphs of FIG. 5 show how this sensitometric response information from two different signal spaces is combined in step 110 to provide an anchor point that serves as a pivotal reference for the transformation mapping between these signal spaces. In this example, a source digital signal space 50 is represented by a histogram of pixel code values (PV), for the anatomy captured on a digital receiver. A target film signal space 60 shows the conventional mapping of optical density (OD) values to log radiation, provided as digitized data. The combination of signal spaces 50 and 60 yields a mapping 70, obtaining a single anchor point $(PV_f, OD_f)$ that maps one value in digital signal space 50 with one value in film signal space 60. (As is described in more detail subsequently, the anchor point can also be represented as $(PV_f, DV_f)$ or as $(PV_{1f}, PV_{2f})$, depending on the signal spaces of interest.)

In embodiments of the present invention, obtaining the best possible results for source→target transformations relates to the task of selecting suitable values for anchor point $(PV_f, OD_f)$.

Turning first to the problem of specifying a suitable source pixel value $PV_f$ it should be noted that there can be a number of ways to do this, including any of the following:
 (a) Choose a statistical value such as the mean or median value of the histogram of the imaged anatomy in a signal space that is logarithmic to the x-ray radiation. In the example of FIG. 5, a point 23b represents a statistical value obtained from histogram data.
 (b) Choose a pixel code value according to the characteristics of the histogram of the imaged anatomy in a signal space that is logarithmic to the x-ray radiation. For example, this may be the value for one of the two ends of the histogram, such as those represented by points 23c and 23d in FIG. 5, or the value corresponding to certain percentage of the distance between the two ends of the histogram.
 (c) Choose the pixel code value corresponding to the tone value of a certain feature of the imaged anatomy. For example, this may be an average value for bone tissue or some value that lies within a range of values for tissue that is of particular interest. In terms of the histogram, this value can be advantageously located at a peak, as represented by a point 23a.
 (d) Choose the pixel code value corresponding to a certain feature of an imaged phantom, such as a step wedge phantom. If this method is used, images of a phantom target must be taken at the same time, typically by placing the phantom near an unused corner of the digital receiver surface.

Once the $PV_f$ value is selected, the target value for a corresponding $OD_f$ or $DV_f$ value is obtained. Overall, a point within the range of $[OD_{min}-OD_{max}]$ is needed for the assignment of $OD_f$. Amid numerous alternative strategies for selecting this value are the following:
 (a.i) $OD_f$ selection can be based on the sensitometry curve of the target screen film system, such as at the point that provides maximum contrast (or at a point that lies within a given range of this value). This value is termed the maximum gamma point in this type of curve. A point 28b represents this point in FIG. 5.
 (a.ii) A mapping $OD_f$ value can be specified based on transition characteristics of the sensitometry curve of the target screen film scanning system relative to radiation level changes. For example, a value that is half-way between $OD_{min}$ and $OD_{max}$ could be chosen, or a value at some percentage level between these extremes, or toe and shoulder points as is represented at points 28a and 28c.
 (a.iii) A mapping $OD_f$ value can be specified based on the linearity of the sensitometry curve of the screen film system relative to the amount of received radiation change.
 (a.iv) A mapping $OD_f$ value can be determined by the optical density of a feature on a phantom, such as a step wedge phantom, that was used to determine $PV_f$, described earlier in (d).

As has been noted, the anchor point may map a digitized value (DV) in order to give the anchor point the form $(PV_f, DV_f)$. In this case, similar strategies as those used for $OD_f$ value selection can apply, including:
 (b.i) A mapping digitized value $DV_f$ can be specified to correspond to the optical density of the sensitometry curve that exhibits the highest contrast (using slope, gradient, or gamma).
 (b.ii) A mapping digitized value $DV_f$ of digitized film that corresponds to the optical density on a selected transition point of the sensitometry curve for the screen film system can be used.
 (b.iii) A mapping digitized value $DV_f$ could be chosen corresponding to the optical density that provides a desired level of linearity of the sensitometry curve.
 (b.iv) A mapping digitized value $DV_f$ could be chosen corresponding to the optical density of a feature on a phantom, such as a step wedge phantom, that was used to determine $PV_f$ in (d).

As FIG. 5 shows in mapping 70 of source signal space to target signal space, the outcome of mapping decisions step 110 (FIG. 3) identifies an anchor point $(PV_f, OD_f)$ in the relation of OD (target signal space) versus PV (source signal space). Where the target signal space has digitized values DV, the outcome of mapping decisions step 110 defines an anchor point $(PV_f, DV_f)$. Where the target signal space has pixel values (PV) from another digital detector, the outcome of mapping decisions step 110 defines an anchor point $(PV_{1f}, PV_{2f})$.

Following step 110 is a transform step 120 that applies the transform for mapping a range of source pixel code values to a corresponding range of target values. This transform includes the anchor point. Calculations for transform step 120 differ based on the response characteristic of the digital receiver, whether linear or logarithmic, as shown and described following.

For Receiver with Linear Response

Referring back to FIG. 3, for digital images from a digital detector system for which the pixel value in the image is linearly proportional to the amount of x-ray radiation, steps 122a, 124a, and 126a are used for generating a transform.

A beta calculation step 122a calculates a β term that will be used subsequently to define the transformation. The value of β for this case is determined by substituting the values of the previously defined anchor coordinate point ($PV_f$, $OD_f$) to obtain:

$$\beta = \log_q PV_f + \frac{1}{c} \times \ln\left(\frac{a}{OD_f - OD_{min}} - b\right) \quad \text{(eq. 3)}$$

where a, b and c are again the fitting constant previously determined by Eq. 1.

Where the mapping optical density coordinate $OD_f$ is selected to provide the highest contrast as described earlier (a.i), or midway between $OD_{min}$ and $OD_{max}$ as described earlier in (a.ii), eq. 3 can be further simplified as $$\beta = \log_q PV_f + \frac{\ln(b)}{c} \quad \text{(eq. 4)}$$

The following equation then converts the pixel values into optical density values provided by the film:

$$OD = OD_{min} + \frac{a}{b + e^{-c(\log_q(PV) - \beta)}} \quad \text{(eq. 5)}$$

where:
a, b and c are the fitting constant from eq. 1;
PV is the pixel value of the digital image;
q is the base of the logarithmic function related to the sensitometric response of the imaging film.

This shows at least some of the significance of anchor point ($PV_f$, $OD_f$) for the balance of the transformation in this case. A mapping step 124a (FIG. 3) then applies eq. 5 to each point in the image data to obtain PV→OD mapping. An optional mapping step 126a provides a further transformation of the optical density to a digital value, that is, OD→DV mapping.

For Receiver with Logarithmic Response

For digital images from a digital detector system for which the pixel value in the image is logarithmically proportional to the amount of x-ray radiation, a proportionality constant S, corresponding to a slope, is computed. Proportionality constant S relates the logarithmic response to the x-ray radiation level for a pixel value PV, using:

$$PV = S \times \log_q(R) + t \quad \text{(eq. 6)}$$

where:
t is an empirically determined intercept value.

A beta calculation step 122b calculates a β term, used subsequently, to define the transformation. The value of β is determined by substituting the values of anchor point coordinates ($PV_f$, $OD_f$) to obtain:

$$\beta = PV_f + \frac{S}{C} \times \ln\left(\frac{a}{OD_f - OD_{min}} - b\right) \quad \text{(eq. 7)}$$

where a, b and c are the same fitting constants previously determined using eq. 1.

In the case of selecting $OD_f$ to provide the maximum contrast, as listed above in (a.i) or half way between $OD_{min}$ and $OD_{max}$, eq. 7 can be further simplified as:

$$\beta = PV_f + \frac{S \times \ln(b)}{c} \quad \text{(eq. 8)}$$

A mapping step 124b then applies the transform of eq. 9 to each point in the image data to obtain PV→OD mapping. This converts a range of pixel values into a corresponding range of optical density values of the film:

$$OD = OD_{min} + \frac{a}{b + e^{-\frac{c}{S}(PV - \beta)}} \quad \text{(eq. 9)}$$

where a, b and c are the fitting constants from eq. 1, S is the proportionality constant used in eq. 6, and PV is the pixel value of the digital image. An optional mapping step 126b provides a further transformation of the optical density to a corresponding digitized value, that is, OD→DV mapping.

Figure 6:
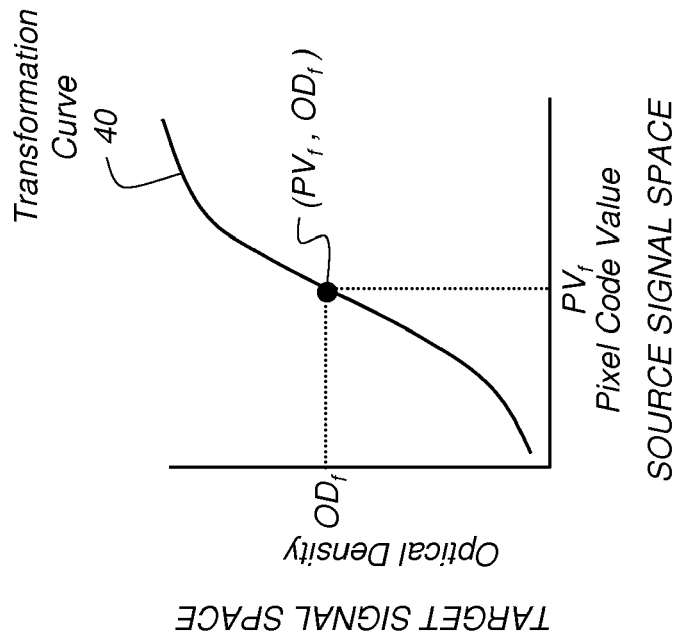
FIG. 6 is a graph showing the transformation curve including the anchor point in one exemplary embodiment.

FIG. 6 shows the transformation curve that maps target signal space to source signal space, including the anchor point ($PV_f$, $OD_f$) in one exemplary embodiment. As this figure shows, any transformation curve 40 that is formed using the method of the present invention necessarily includes anchor point ($PV_f$, $OD_f$), but may vary from other possible transform curve solutions, adjusted by shifting in vertical or horizontal position or slightly modified in shape, such as by adjustment to the slope of the curve through this anchor point. It should also be observed that anchor point ($PV_f$, $OD_f$), may be located at any suitable point along transformation curve 40, including at a point that is in a high ("toe") or low brightness ("shoulder") region where the curve has a sigmoid shape.

Figure 7:
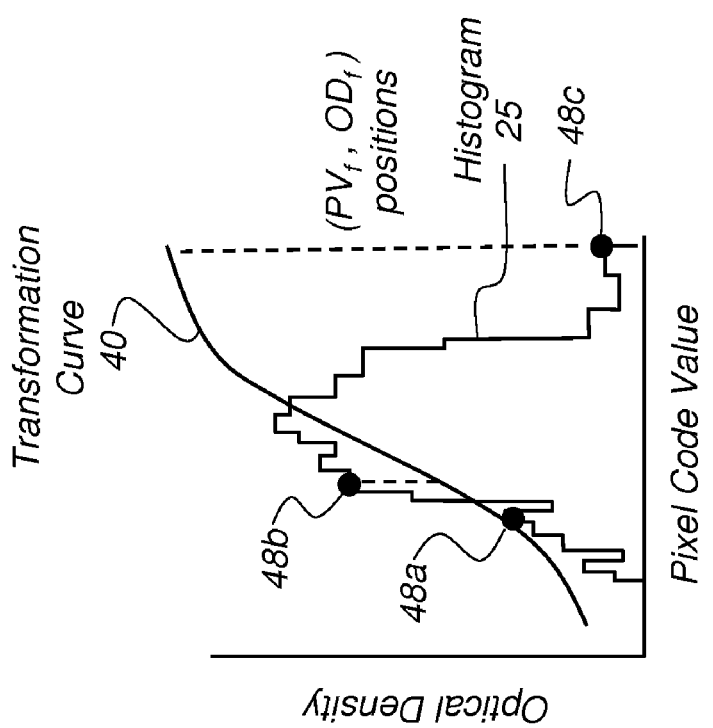
FIG. 7 is a graph of an example image histogram superimposed on a transformation curve and showing possible anchor points.

The graph of FIG. 7 shows a histogram 25 of an anatomy radiographic image data, superimposed on the transformation curve 40 in order to relate the source values in the histogram (horizontally arranged) with "remapped" or "transformed" target values. Different points 48a, 48b, and 48c demonstrate how the anchor point ($PV_f$, $OD_f$) could be located along the transformation curve and relative to histogram 25. Central point 48b might be, for example, a mean or median point in histogram 25 mapped to the OD value that has the maximum gamma. Point 48a might be the pixel code value of the peak in histogram 25 mapped to the OD value that is at 25% level of the difference between $OD_{max}$ and $OD_{min}$, above the $OD_{min}$. Points 48c might be the maximum pixel code value of the image data that is mapped close to the shoulder region of the sensitometric curve.

In another example embodiment, mapping of image data is between two digital receivers, one as the image source, one as the target. This sequence parallels the logic flow of FIG. 3, but with the necessary adaptations to transform step 120 for performing the mapping identified earlier as (iii) PV space (system #1)→PV space (system #2).

Similar to the logic flow diagram of FIG. 3, setup step 100 obtains sensitometric response data for source and target signal spaces. In this example, digital receiver 1 is the target, having a logarithmic response to the amount of radiation. Digital receiver 2, with a linear response to the amount of radiation, is the source imaging modality.

The response function for target digital receiver 1 is as follows:

$$PV = a \times \log_q R + b \quad (\text{eq. 10})$$

wherein $PV_1$ is the pixel value from the digital receiver and parameters a and b again relate to the fitting function.

Continuing to mapping decisions step 110 in FIG. 3, a pixel value from the source digital receiver 2 is selected to be correlated to a pixel value from the target digital receiver 1, forming anchor coordinate point ($PV_{2f}$, $PV_{1f}$). The method used in selecting the $PV_{1f}$, $PV_{2f}$ values can be similar to the method described earlier using histograms of the imaging anatomy from both the source and target digital receivers. A beta β value can then be calculated for the transformation, using:

$$\beta = PV_{1f} - a \times \log_q PV_{2f} \quad (\text{eq. 11})$$

A mapping step follows for transforming each pixel value $PV_2$ from digital receiver 2 into the pixel value $PV_1$ from digital receiver 1, using the transform:

$$PV_1 = a \times \log_q PV_2 + \beta \quad (\text{eq. 12})$$

The image data mapping method of the present invention can also be used for normalization, so that images obtained from different systems or modalities can be visually reconciled with each other for comparison. For normalization, an image of a step wedge or other suitable standard image could optionally be obtained for each type of imaging apparatus to be normalized. This standard image target or phantom would be imaged along with the image to be re-mapped. Mapping algorithms for each device would then have the same reference anchor point ($PV_f$, $OD_f$), with corresponding adjustments for amount of change with changed radiation and a suitable offset value.

The invention has been described with reference to a subset of possible embodiments. However, it will be appreciated that variations and modifications can be effected by a person of ordinary skill in the art without departing from the scope of the invention. For example, various techniques could be employed for identifying a suitable anchor point ($PV_f$, $OD_f$) or ($PV_f$, $DV_f$) or ($PV_{1f}$, $PV_{2f}$) for conversion between systems. While a number of transforms and equations are given in this disclosure, it should be emphasized that any of a number of alternate transforms could be used for transforming or mapping radiological image data from a system to the target system, substituted for those shown in equations 4-12.

Thus, what is provided is a method for mapping image data between different radiographic imaging systems.

PARTS LIST

- 23*a*, 23*b*, 23*c*, 23*d*. Point
- 25. Histogram
- 28*a*, 28*b*, 28*c*. Point
- 30. Sensitometric response curve
- 40. Transformation curve
- 48*a*, 48*b*, 48*c*. Point
- 50. Source digital signal space
- 60. Target film signal space
- 70. Mapping
- 100. Setup step
- 105. Normalization step
- 110. Mapping decisions step
- 120. Transform step
- 122*a*, 122*b*. Beta calculation step
- 124*a*, 124*b*. Mapping step
- 126*a*, 126*b*. Mapping step

The invention claimed is:

1. A method for mapping radiological image data from a source imaging system to a different target imaging system, executed at least in part by a computer, comprising:
   obtaining sensitometric response data for both the source and the target imaging systems;
   identifying an anchor point that relates a specified source signal value to a specified target signal value;
   applying a transform to map a range of source signal values the image data to a corresponding range of target signal values, wherein the transform is defined according to the sensitometric response data obtained for both the source and the target imaging systems and according to the identified anchor point; and
   using the transformed target signal values of the image data for display and/or analysis.

2. The method of claim 1 wherein the target imaging system uses scanned data obtained from a photosensitive medium.

3. The method of claim 1 wherein identifying the anchor point comprises obtaining either a source value or a target value, or both a source value and a target value from a histogram of imaged anatomy.

4. The method of claim 1 wherein identifying the anchor point comprises obtaining either a source value or a target value, or both a source value and a target value, corresponding to the tone value of a certain feature of imaged anatomy.

5. The method of claim 1 wherein identifying the anchor point comprises obtaining either a source value or a target value, or both a source value and a target value, corresponding to the tone value of a certain feature of an imaged phantom.

6. The method of claim 1 wherein the source and target imaging systems are digital imaging systems.

7. The method of claim 6 further comprising normalizing the data range for source and target imaging systems.

8. A method for mapping radiological image data from a source imaging system using a source digital receiver to a different target imaging system using a target digital receiver, executed at least in part by a computer, comprising:
   obtaining sensitometric response data for both source and target imaging systems;
   identifying an anchor point by correlating a digital value $PV_{1f}$ from the target imaging system with a corresponding digital value $PV_{2f}$ from the source imaging system;
   applying a transform to map a range of source signal values of the digital data to a corresponding range of target signal values, wherein the transform is defined according to the sensitometric response data obtained for both the source and the target imaging systems and includes the identified anchor point; and
   using the transformed target signal values of the image data for display and/or analysis.

* * * * *

UNITED STATES PATENT AND TRADEMARK OFFICE
CERTIFICATE OF CORRECTION

PATENT NO. : 8,199,995 B2  Page 1 of 1
APPLICATION NO. : 12/021504
DATED : June 12, 2012
INVENTOR(S) : Yang et al.

It is certified that error appears in the above-identified patent and that said Letters Patent is hereby corrected as shown below:

Column 10, line 9, delete "The invention claimed is." replace with -- Claims: --.

Signed and Sealed this
Twenty-first Day of August, 2012

David J. Kappos
*Director of the United States Patent and Trademark Office*